United States Patent [19]
Rubin

[11] Patent Number: 5,910,124
[45] Date of Patent: Jun. 8, 1999

[54] VENTRICULAR ASSIST DEVICE AND METHOD

[75] Inventor: Leo Rubin, Suffern, N.Y.

[73] Assignee: Cardiassist Incorporated, Suffern, N.Y.

[21] Appl. No.: 09/004,435

[22] Filed: Jan. 8, 1998

Related U.S. Application Data

[63] Continuation-in-part of application No. 08/652,522, filed as application No. PCT/US95/00184, Jan. 9, 1995, Pat. No. 5,707,336, which is a continuation-in-part of application No. 08/179,153, Jan. 10, 1994, abandoned.

[51] Int. Cl.$^6$ .............................. A61H 7/00; A61H 19/00
[52] U.S. Cl. ................................................ 601/153; 600/16
[58] Field of Search ........................... 601/153; 607/129, 607/122; 623/3; 606/191; 600/16, 17

[56] References Cited

U.S. PATENT DOCUMENTS

| | | |
|---|---|---|
| 3,371,662 | 3/1968 | Heid et al. . |
| 3,496,932 | 2/1970 | Prisk et al. . |
| 3,587,567 | 6/1971 | Schiff . |
| 3,613,672 | 10/1971 | Schiff ...................................... 601/153 |
| 3,730,186 | 5/1973 | Edmunds, Jr. et al. . |
| 3,860,968 | 1/1975 | Shapiro . |
| 4,048,990 | 9/1977 | Goetz . |
| 4,192,293 | 3/1980 | Asrican . |
| 4,595,000 | 6/1986 | Hamou . |
| 4,597,381 | 7/1986 | Oumi et al. . |
| 4,690,134 | 9/1987 | Snyders . |
| 4,848,364 | 7/1989 | Bosman . |
| 5,098,369 | 3/1992 | Heilman et al. . |
| 5,131,905 | 7/1992 | Grooters . |
| 5,169,381 | 12/1992 | Snyders . |
| 5,256,132 | 10/1993 | Snyders . |
| 5,385,528 | 1/1995 | Wilk . |
| 5,749,839 | 5/1998 | Kovacs ..................................... 601/153 |

FOREIGN PATENT DOCUMENTS 2645739  10/1990  France .

OTHER PUBLICATIONS

Anstadt, Mark P. and George L. and Lowe, James E., "Direct mechanical ventricular actuation: A review", Resuscitation, 21(1991), pp. 7–23, Elsevier Scientific Publishers Ireland Ltd.

Feindt, P. et al., "The Concept of 'Direct Mechanical Ventricular Assistance' in the Treatment of Left–Ventricular Failure," Part 1, Thorac, cardiovasc. Surgeon 43 (1995), pp. 1–12.

*Primary Examiner*—Richard J. Apley
*Assistant Examiner*—Justine R. Yu
*Attorney, Agent, or Firm*—Baker & Botts, L.L.P.

[57] ABSTRACT

Cardiac ventricular assist apparatus adapted to be placed by insertion through an incision in the wall of the upper abdomen below the rib cage and an incision in the inferior aspect of the pericardium proximate the heart apex comprises a flexible bladder assembly that adapted to be passed through the incision in the pericardium to a position between the pericardial sac and the epicardium. The bladder assembly is of a size such and shape such as to be engageable with a substantial portion of the outer surface of the left ventricle of a heart. The bladder assembly includes a distensible pumping bladder that is attached to a tube through which a gas can be introduced into it to compress the left ventricle and withdrawn from it to allow the ventricle to fill and a non-distensible retaining bladder, which is substantially coextensive with the pumping bladder and receives a packed body of particulate material.

15 Claims, 8 Drawing Sheets

VENTRICULAR ASSIST DEVICE AND METHOD

REFERENCE TO PRIOR APPLICATIONS

The present application is a continuation-in-part of application Ser. No. 08/652,522, filed Jun. 4, 1996, U.S. Pat. No. 5,707,336, which was the national stage of PCT International application No. PCT/US95/00184, filed Jan. 9, 1995, International Publication Number WO 95/18953, now abandoned, which in turn was a continuation-in-part of application Ser. No. 08/179,153, filed Jan. 10, 1994, and entitled VENTRICULAR ASSIST DEVICE, now abandoned.

BACKGROUND OF THE INVENTION

Several forms of heart failure can be treated by ventricular assistance, such as by closed chest compression (an aspect of cardiopulmonary resuscitation), manual heart message, or mechanical ventricular assistance. Closed chest compression, coupled with medication, must be stopped and replaced by some other treatment if effective rhythm and adequate blood flow are not restored expeditiously. Similarly, while manual heart message can be performed for an indefinite period, it is impractical to do so. Manual message also requires a thoracotomy, with its own morbidity, high cost, and potential complications.

Direct mechanical ventricular assistance has been the subject of considerable research for many years. The requirements for highly specialized equipment and major surgery for implantation has limited widespread applicability, especially in emergency situations.

Maintenance of blood circulation by a failing heart can also be provided by removing blood from the ventricles and pumping it back to the aorta. Indirect mechanical ventricular assistance, like direct assistance, requires extensive surgery. It also involves direct contact between the blood and the apparatus. Blood can clot in areas of the apparatus where flow rates are low, and clots can break away and cause a stroke.

Direct mechanical ventricular assist devices have been described in the medical literature and in patents, the following being exemplary:

U.S. Pat. No. 2,826,193 (Vineberg, 1958)
U.S. Pat. No. 3,034,501 (Hewson, 1962)
U.S. Pat. No. 3,233,607 (Bolie, 1966)
U.S. Pat. No. 3,371,662 (Heid et al., 1968)
U.S. Pat. No. 3,455,298 (Anstadt, 1969)
U.S. Pat. No. 3,496,932 (Prisk et al., 1970)
U.S. Pat. No. 4,048,990 (Goetz, 1977)
U.S. Pat. No. 4,690,134 (Snyders, 1987)
U.S. Pat. No. 5,131,905 (Goofers, 1992)
U.S. Pat. No. 5,169,381 (Snyders, 1992)
U.S. Pat. No. 5,256,132 (Snyders, 1993)
U.S. Pat. No. 5,385,528 (Wille, 1995).

"First Successful Bridge to Cardiac Transplantation Using Direct Mechanical Ventricular Actuation," J. E. Lowe et al., Ann Thorac Surg 1991; 52:1237–45

"Direct Mechanical Ventricular Actuation: A Review," M. P. Anstadt et al., Resuscitation, 1991; 21:7–23

"The Concept of Direct Mechanical Ventricular Assistance in the Treatment of Left-Ventricular Failure," P. Feindt et al., Thorac. cardiovasc. Surgeon 43 (1995:1–12

Most of the devices proposed heretofore for direct mechanical ventricular actuation are implaced by performing a thoracotomy, opening a window in the pericardium, and placing a cup-like squeezing element over the ventricles. The squeezing element typically has a rigid or semi-rigid outer cup and two chambers, one for each ventricle, formed by panels of an extensible material attached and sealed to the outer cup. The chambers are periodically inflated with a gas under pressure supplied through a tube leading from a mechanical pump to squeeze the ventricles and discharge blood (systole) and then deflated by evacuation by the mechanical pump to draw blood from the atria (diastole).

The squeezing action of the chambers requires that the outer non-extensible cup-like wall member of the squeezing device sustain the reaction loads of the pressure applied to the heart. That means, in turn, that the element must be sized and shaped to fit the heart snugly. Inasmuch as the exact size of the patient's heart is often not known in advance, it is necessary to have a range of sizes of squeezing elements on hand for selection and use after access to the heart has been obtained. While the need to maintain an inventory of squeezing elements and for measuring the heart and selecting an element of the right size is by no means an insurmountable impediment to clinical use of such devices, it is an inconvenience and delays the operative procedure. In an emergency situation, such as heart arrest during surgery, time is critical. The sooner that normal or near normal blood flow can be restored, the lower is the probability of irreversible damage to the patient due to temporary loss of cardiac function.

Because the ventricular portion of the heart is roughly conical, the squeezing action of the squeezing element against the ventricles tends to push the element away from the heart. Thus, it is necessary to hold the element in place. Anstadt et al. (referred to above) provide retention of the element by applying a vacuum within the squeezing element. Snyders (also referred to above) provides retention by suturing the squeezing element to the pericardium.

In addition to the requirement for highly invasive surgery for implanting the device and the need for closing the pericardium window and the thoracotomy wound if the device is to be left in place for a significant period of time, which will almost always be the case, reoperation is required to remove it. Both the operation to implant the assist device and the operation, if required, to remove it place the patient at additional risk beyond the heart condition that called for its use. Even if thoracotomy is not required for removal of the device, as proposed by Goetz (referred to above), surgical implantation of previously known mechanical ventricular assist devices requires relatively complicated surgery that offers little chance for success unless performed by a skilled surgical team in an operating room.

Snyder's '132 and Wilk '528 propose implanting a heart assist device endoscopically, i.e., by inserting the device through an introducer tube that passes through a small incision in the pericardium. The incision is made with the aid of a light source and video imaging equipment for locating the site of the incision and a suitable cutting instrument for making the incision. The assist devices, like those described and shown in other references, are cup-like or cuff-like and thus surround both ventricles and squeeze both ventricles.

The present inventor believes that squeezing both ventricles is inadvisable and may actually be deleterious. That belief is supported by the results of research reported by P. Feindt et al. (cited above).

SUMMARY OF THE INVENTION

One objective of the present invention is to provide ventricular assist apparatus that includes a flexible, inflatable bladder that can be placed in contact with the heart with minimally invasive surgery that can be carried out quickly. Another objective is to provide assistance only to the left ventricle. It is also an objective to provide ventricular assist apparatus that can be surgically placed in settings other than a hospital operating room, such as in a hospital emergency room or an emergency coronary care vehicle. Still another objective is to provide a method of providing ventricular assistance to a failing heart, which can be used for both a relatively short period of time to support blood circulation following a cardiac arrest or a relatively long period of time to maintain heart function while a damaged heart heals or until a replacement heart for transplantation becomes available.

The foregoing objects are attained, in accordance with one aspect of the present invention, by a cardiac ventricular assist apparatus adapted to be placed by insertion through an incision in the wall of the upper abdomen below the rib cage and an incision in the inferior aspect of the pericardium. The apparatus includes a bladder assembly having walls of flexible material, the bladder assembly being of a size and shape such as to be engageable exclusively with a substantial portion of the outer surface of the left ventricle of a heart and having a distal edge of a length such as to extend around the heart proximate to the atrio-ventricular groove through an angle of from about 180 degrees to about 270 degrees from one end near the pulmonary artery to another end near the inferior vena cava. The bladder assembly is adapted to be passed in a collapsed condition through the incision in the pericardium to a position between the pericardial sac and the epicardium and includes a first bladder having an inner wall engageable with the heart and a second bladder attached to and substantially coextensive with the first bladder, at least one wall of the second bladder being substantially non-extensible so as to provide dimensional stability to the bladder assembly circumferentially and axially of the heart. A tube attached to the first bladder permits a gas to be introduced into and withdrawn from the first bladder cyclically so as to apply pumping assistance to the left ventricle and allow the ventricle to fill with blood between each pumping stroke of the first bladder. A tube attached to the second bladder provides for the introduction of a fluid material into the second bladder to render the second bladder substantially rigid and to conform the bladder assembly to the shape of the left ventricle. The fluid material may be a particulate material that is introduced into the second bladder entrained in a gas and is made rigid by withdrawing at least part of the gas from the second bladder so that the particulate material becomes packed.

The first bladder provides pumping assistance to the left ventricle. The second bladder, which is rendered semi-rigid by the fluid substance introduced into it, and the pericardium provide support for the reaction forces due to the pumping pressure of the first bladder and, by virtue of conforming to the shape of the portion of the heart engaged by the bladder assembly, keeps the assembly in position in engagement with the left ventricle. The second, semi-rigid bladder of the assembly is also connected to the tube by which it is filled. The tube can be suitably held in place outside the patient's body, thereby holding the second bladder in position against being forced downwardly away from the heart apex.

Preferably, the first bladder has an inner wall of an elastically extensible material attached along an outer perimeter to the wall of non-extensible material of the second bladder. The elasticity of the inner wall of the first bladder may be greater in a portion adjacent the distal end of the assembly than in a portion adjacent a proximal end of the bladder assembly such that a proximal portion of the first bladder enlarges before a distal portion and the assembly exerts an enhanced pumping action on the left ventricle that is directed upwardly toward the left ventricular outflow tract.

In preferred embodiments, the first and second bladders have walls that are configured as segments of conical surfaces that approximately match the shape of the part of the heart that the bladder assembly engages without wrinkling.

According to another aspect of the present invention, the first and second bladders have a common posterior lateral edge positioned to reside adjacent the posterior margin of the left ventricle, and the bladder assembly has a third narrow elongated bladder having a proximal portion attached to a proximal portion of the posterior lateral edge of the first and second bladders. The third portion is shaped and configured to be received in the oblique sinus of the heart. A tube attached to the third bladder provides for introducing a fluid into the third bladder so as to expand the third portion into engagement with the oblique sinus and impede circumferential displacement of the bladder assembly relative to the heart. The fluid remains in the third bladder as long as the bladder assembly remains in the patient.

Devices that are ancillary to the bladder assembly and are used in placing it in a patient's body include:

An introducer tube and an inserter wire adapted to be passed through the introducer tube and having a distal end attached to the distal edge of the bladder assembly and having a length such that it is adapted to extend out of the proximal end of the introducer tube for manipulation to move the bladder through the incision in the pericardium and into position between the epicardium and the pericardium;

A light-transmitting cable received through the introducer tube for conducting light through the introducer tube to illuminate a portion of the pericardium;

An image receptor and cable received through the introducer tube for transmitting an image of the illuminated portion of the pericardium through the introducer tube to its proximal end.

Those devices, and perhaps others, together with the bladder assembly, can be provided as a disposable emergency kit and used with a light source, a CCD camera, a television monitor, pumping and vacuum apparatus, a heart monitor, and a defibrillator, which are part of a cardiac emergency care unit. Such a unit may be kept in a surgical suite, an emergency room, or a mobile cardiac emergency vehicle, for example. The apparatus of the present invention can be used not only by physicians but by well-trained paramedics and nurses.

Advantageously, a sensing/pacing electrode and a defibrillator electrode are attached to a wall of the bladder assembly that engages the heart.

The present invention also provides a method for rendering mechanical assistance to a failing heart that includes the following steps:

making an incision in the upper abdomen of a cardiac patient inferior to the xiphoid process and medial to the border of the left coastal arch;

inserting an introducer tube through the abdominal incision;

guiding the introducer tube to a position proximate to the medial aspect of the heart apex;

illuminating a portion of the pericardium proximate to the medial aspect of the heart apex and forming on a monitor an image of said portion;

making an incision in said portion of the pericardium;

providing in collapsed condition a bladder assembly of the type described above;

moving the collapsed bladder assembly through the pericardial incision and guiding it along the heart to a predetermined position, such as by manipulation of an inserter wire;

deploying the collapsed bladder assembly to engage it with the left ventricle;

introducing a fluid material, such as a particulate material entrained in a gas, into the second bladder through the second tube so as to render the second bladder semi-rigid; and repeatedly pumping a gas under pressure into the first bladder and withdrawing the gas from the first bladder to compress and release the left ventricle.

When the bladder assembly has the third narrow elongated bladder that is received in the oblique sinus of the heart, the method also includes the step of introducing a fluid into the third bladder so as to expand the third bladder into engagement with the oblique sinus.

The bladder of the present invention functions by compressing the left ventricle when gas under pressure is introduced into the bladder to expand it. The pericardium, which is intact except for a small incision, and the semi-rigid second bladder of the bladder assembly sustain the reaction load exerted by the inflated bladder. The acting load of the distended bladder collapses the left ventricle. Because the pericardium has a corset-like relationship to the heart, it sustains the reaction load of the bladder. The bladder stays in place between the pericardium and heart, inasmuch as the pericardium remains essentially intact except for the small incision required to allow it to be introduced.

The volumes of the bladder at the ends of heart systole and diastole can be controlled by the gas pump that inflates and deflates the bladder. Accordingly, if the heart is abnormally enlarged (distended), the device enables its size at the end of diastole to be reduced. It is well known that a distended heart pumps less efficiently that a normal sized heart, and the apparatus provides for enhancing the pumping efficiency of a distended heart. Similarly, the volume of the bladder at the end of systole can be established by control of the pump to establish optimal contraction and blood circulation rates.

An important advantage of the device of the present invention is its ability to support blood circulation mechanically without highly invasive surgery, such as open cardiac massage (which requires an emergency thoracotomy) or placement of a mechanical assist device (such as a left ventricular assist device). The only surgical wounds are a relatively small incision in the abdomen and a small incision in the pericardium. The abdominal incision is easily closed; the pericardial incision is left open. The potential for complications in the healing of the wounds is significantly less than more major procedures. The surgery is, of course, vastly easier to perform and can be performed quickly. The assist apparatus can be left in place in the patient for long periods of time, if needed. Removal of the bladder is also simple, inasmuch as it can be pulled out of the pericardium through the small incision through which it was placed. Before withdrawing the bladder, a vacuum is applied to the outer bladder to suction out the particulate material. The device does not directly contact the blood. Accordingly, the risk of clotting in the assist apparatus, which is a problem with blood pumps, is totally avoided.

For a better understanding of the invention, reference may be made to the following description of exemplary embodiments, taken in conjunction with the accompanying drawings.

DESCRIPTION OF THE EMBODIMENTS

Figure 1:
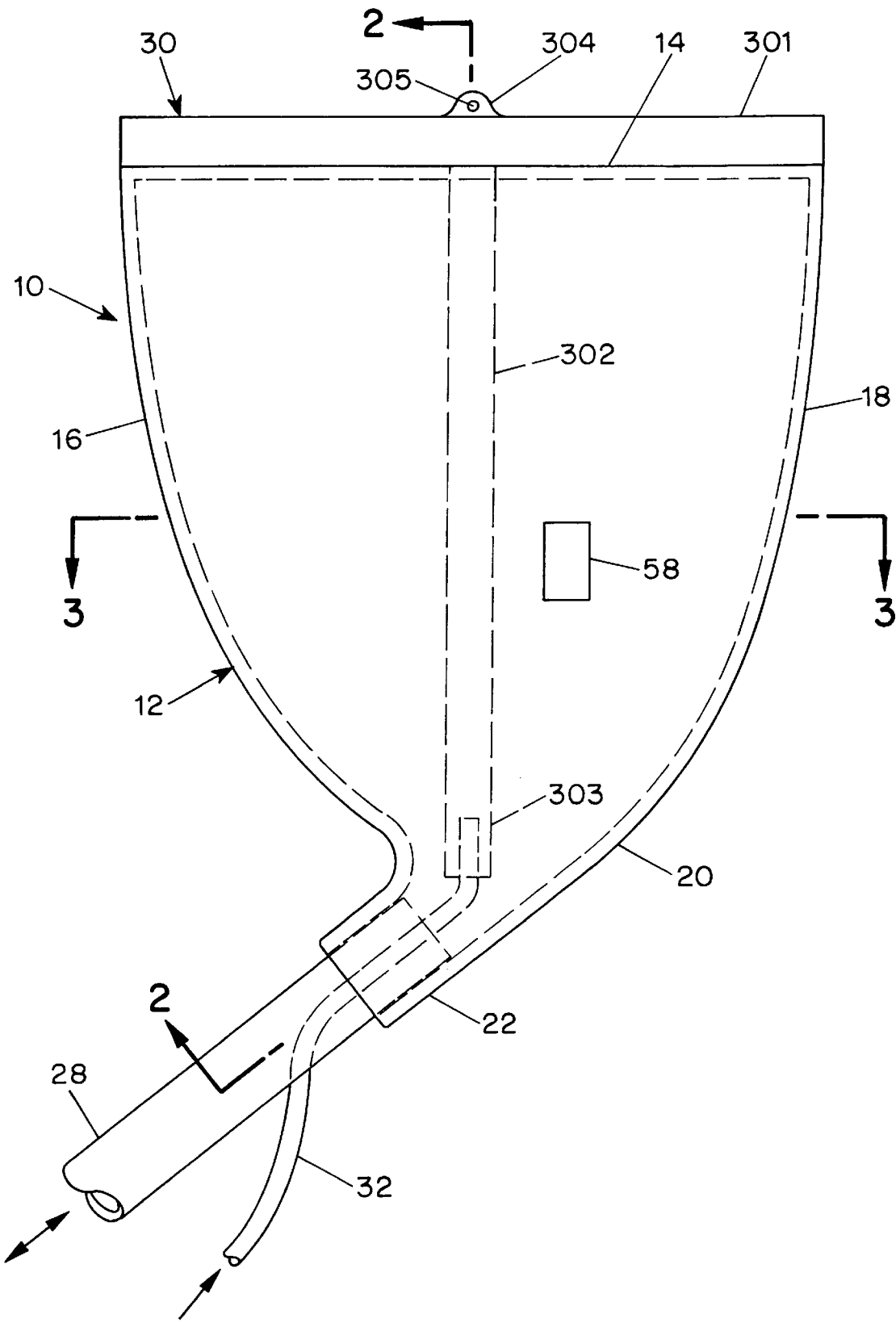
FIG. 1 is a plan view of one embodiment of a bladder.
Figure 2:
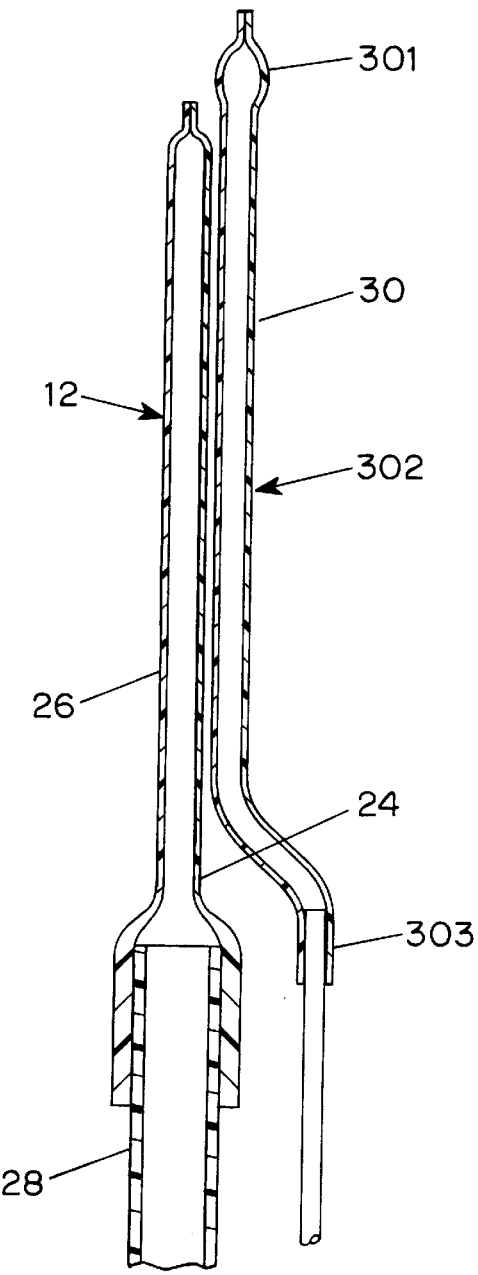
FIG. 2 is a cross-sectional view of the bladder of FIG. 1 taken along a broken plane indicated by the lines 2—2 of FIG. 1.
Figure 3:
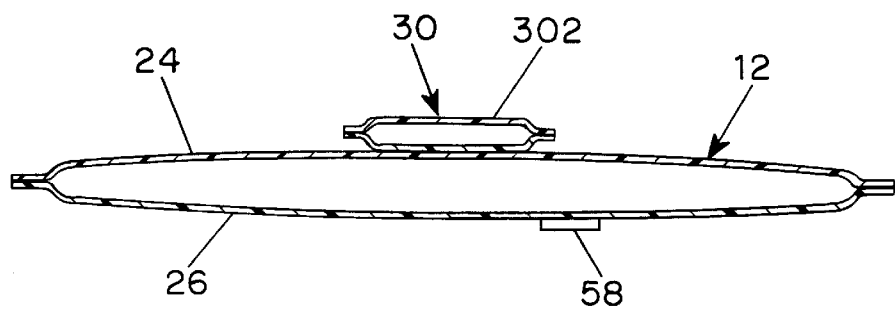
FIG. 3 is a cross-sectional view of the bladder of FIG. 1 taken along lines 3—3 of FIG. 1.

The apparatus 10 shown in FIGS. 1 to 3 includes an inflatable bladder 12 that is made of suitable thin flexible sheet materials that are biologically acceptable for placement in the body. In the flattened condition shown in FIG. 1, the bladder 12 is roughly triangular, having a distal edge 14 that is of a length such that when in place it extends circumferentially around the superior portion of the left ventricle of the heart at a position proximate to the atrioventricular groove through from about 180 degrees to about 270 degrees, one end being located near the pulmonary artery and the other end near the inferior vena cava. The side edges 16 and 18 are curved and are of a length such that when the bladder is in place in engagement with the heart, the proximal apex 20 is located slightly inferiorly of the heart apex. Because the bladder is placed against the heart through an incision at the inferior aspect of the pericardium proximate to the heart apex, the proximal end portion 22 of the bladder leads off somewhat laterally with respect to the vertical axis of the triangle, i.e., in the medial direction anatomically with respect to the heart as viewed from the front.

The bladder is composed of two sheets 24 and 26 of thin, highly flexible sheet material (see FIGS. 2 and 3) joined together along their edges. The sheet 24 is non-extensible, and the sheet 22 is extensible. Accordingly, when inflated, the bladder expands predominantly in a direction perpendicular to the sheets. The sheets are fabricated so that they form conical surfaces that approximately match the shape of the part of the heart that the bladder engages without wrinkling to any great extent. The proximal end portion 22 of the bladder receives and is joined in sealed relation to a length of moderately flexible tubing 28.

The cross-piece portion 301 of a T-shaped tube 30 is attached to the distal edge 14 of the bladder. The leg portion 302 of the tube extends along the triangle axis of the bladder and is preferably attached to the adjacent wall of the bladder along most of its length. The tube is made from T-shaped blanks of a thin, highly flexible non-distensible material joined along their edges. The proximal end 303 of the leg 302 receives and is affixed in sealed relation to a length of moderately flexible tubing 32. A tab 304 having a hole 305 is formed on the edge of the cross-piece portion of the tube 300 and serves as an attachment point for an inserter wire, as described below.

Figure 5:
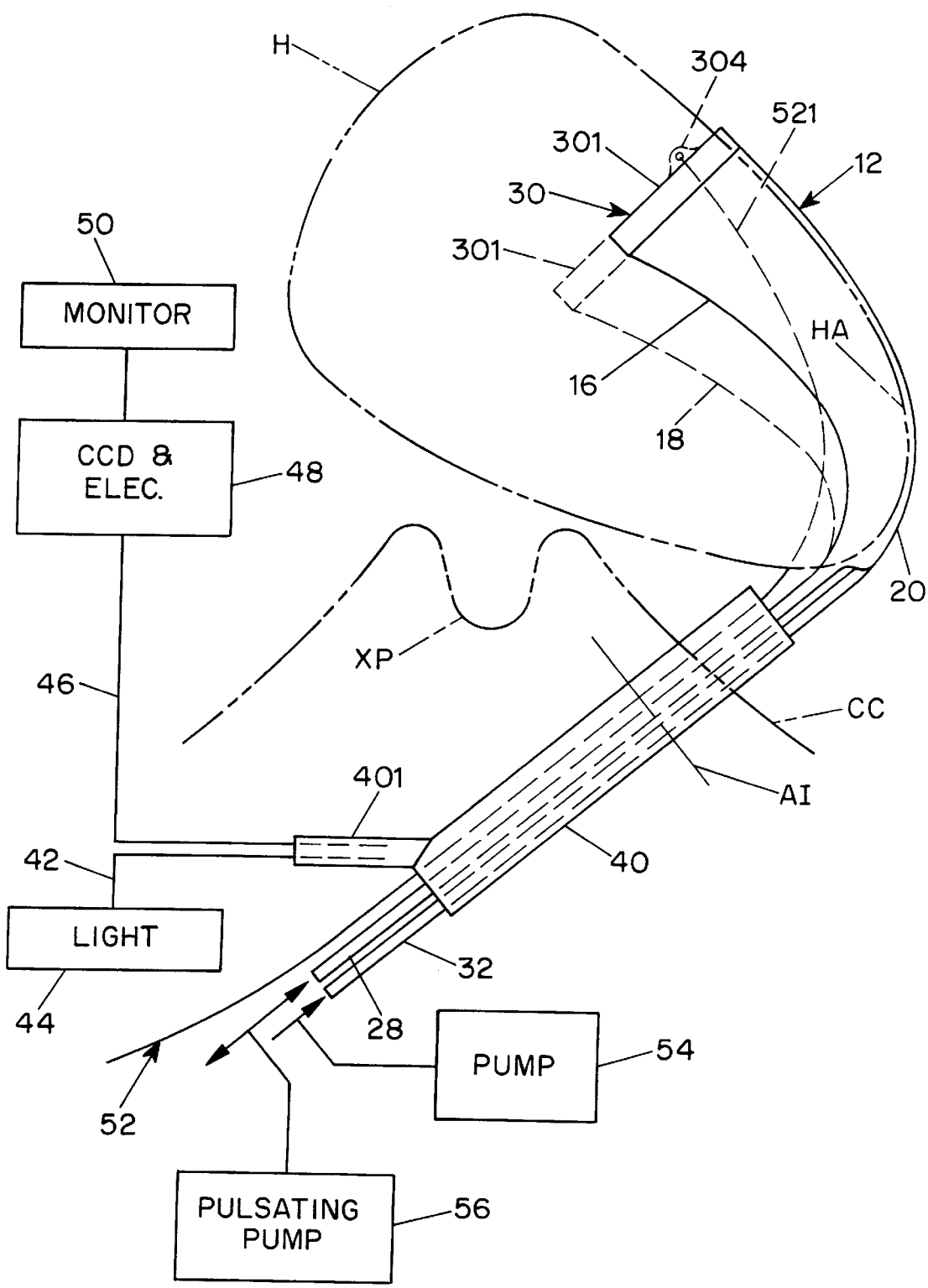
FIG. 5 is a schematic drawing showing other components used in the invention and the use of the invention in a patient.

Referring to FIG. 5, the bladder is placed in engagement with the heart H by minimally invasive surgery. An incision AI about 3 cm long is made in the upper abdomen inferiorly of the xiphoid process XP and medially of the borders of the left coastal arch CA. An introducer tube 40 having a diameter of about 2.5 cm to 3.0 cm is inserted through the abdominal incision AI and is guided to a position proximate to the medial aspect of the heart apex HA. A lateral branch 401 of the tube 40 receives the proximal end portion of a light conductor 42 that leads from a light source 44 and the proximal end portion of an image conductor 46 that leads to a CCD camera and electronics unit 48. The distal end of the light conductor 42 illuminates the path of the introducer as it is being inserted and ultimately illuminates a portion of the pericardium proximate to the medial aspect of the heart apex HA. A lens (not shown) at the distal end of the image conductor 48 receives an image, which is picked up by the camera and is processed to present the image on a monitor 50.

Using a grasping instrument and special scissors that have blades that are presented parallel to the surface of the pericardium, which are inserted through the introducer tube 40, an incision about 2.0 to 2.5 cm long is cut in the medial aspect of the pericardium proximate to the heart apex HA.

The bladder is supplied carefully folded into a collapsed condition, much like a fan, within a placement tube (not shown) and has the distal end 521 of an insertion wire 52 attached to the eye 304 of the bladder. This unit is inserted through the introducer tube 40 and through the incision in the pericardium. The placement tube is removed, and the proximal end of the inserter wire 52 is manipulated to guide the still collapsed bladder along the posterior aspect of the heart both laterally and superiorly. The light and imaging apparatus are used to observe the path of the inserter wire 52. Manipulation of the part of the tube 28 outside the introducer tube enables the apex of the bladder to be placed slightly inferiorly of the heart apex.

When the bladder has reached the desired position, the tube 32 is attached to a source of gas pressure, such as a hand or manual pump 54 having a reservoir of an inert gas, such as $CO_2$, and gas pressure is applied to the tube 30. The inflation of the tube causes it to extend and push the distal portion of the bladder circumferentially part way around the heart. The tube 28 is connected to a pulsating pump 56 which alternately pumps a gas, such as CO2, into the bladder and suctions the gas back out. The pump may be controlled by ECG signals of the rhythm of the heart if the heart rhythm is regular or by signals from a heart pacer if it is not. To this end, it is advantageous to attach a sensing/pacing electrode 58 to the wall 26 of the bladder that engages the heart. The electrode serves the alternative functions of sensing the heart rhythm when it is regular and of pacing the heart when the rhythm is slow. In either case, the operation of the pump is controlled by signals derived from or delivered to the electrode 58. The pulsating expansion and contraction of the bladder alternately compresses the left ventricle, to deliver blood, and releases it to allow it to fill. The reaction loads of the bladder are borne by the still intact pericardium.

In some patients, it may be beneficial to introduce a second bladder into the pericardium in a position to engage the right ventricle. The second bladder is inflated and deflated in synchronization with the bladder that engages the left ventricle. The tandem operation of the two bladders, which preferably substantially completely surround the ventricular portion of the heart, provides enhanced assistance to the heart muscles, as compared with a single bladder working mainly the left ventricle, and permits better control of both the pulmonary and systemic circulations by proportioning of the pumping displacements of the two bladders.

Figure 4:
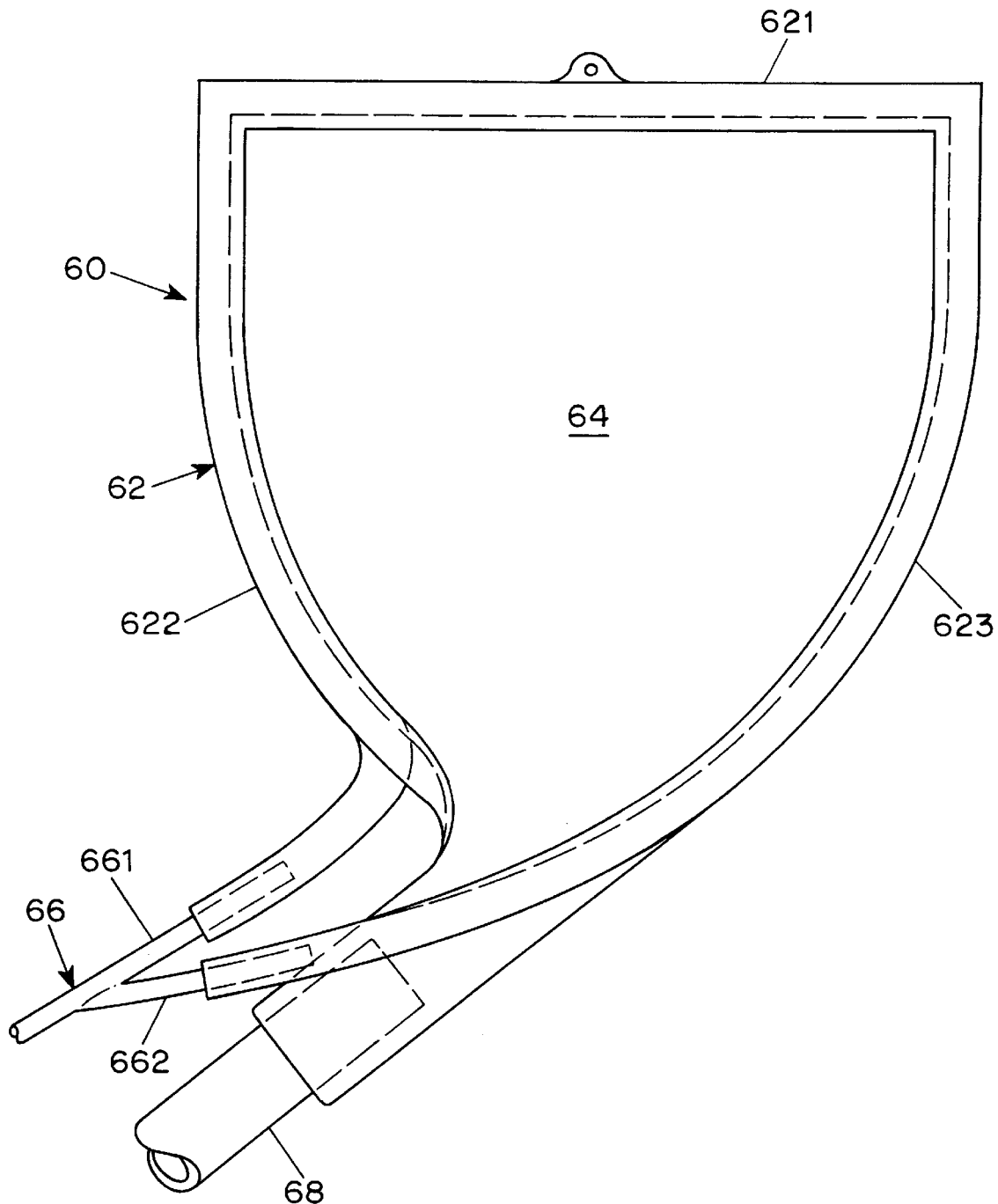
FIG. 4 is a plan view of a second embodiment of a bladder.

The bladder 60 shown in FIG. 4 is essentially the same as the bladder shown in FIGS. 1 to 3, except that it has a non-distensible tube 62 having a distal portion 621 that extends along and is joined to the distal margin of an inflatable bladder 64 and side portions 622 and 623 that extend along and are joined to the respective side margins of the bladder. The ends of the respective side portions 622 and 623 of the non-distensible tube 62 are joined and sealed to branch portions 661 and 662 of a gas supply tube 66, through which a gas under pressure is delivered to inflate the tube 62 and extend the bladder after it has been placed between the pericardium and the heart. A pulsating gas pressure is supplied through a tube 68 joined and sealed to the bladder.

Figure 6:
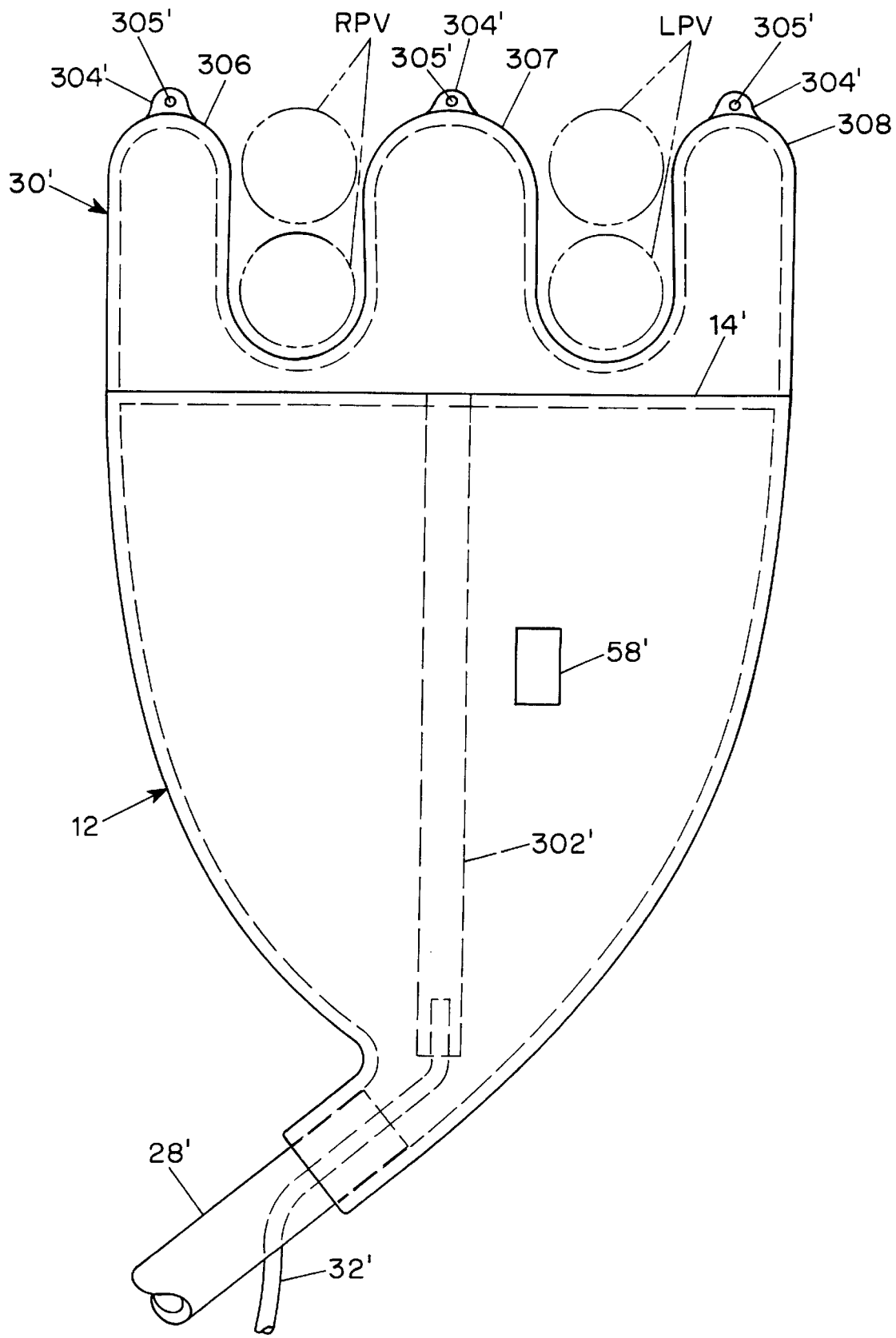
FIG. 6 is a plan view of a third embodiment of a bladder.

The bladder shown in FIG. 6 is similar to the one shown in FIGS. 1 to 3. Accordingly, the same reference numerals are applied, but with a prime suffix to differentiate the embodiment of FIG. 6. The embodiment of FIG. 6 differs from that of FIGS. 1 to 3 in that it has a non-extensible tube 30' having three finger portions 306, 307 and 308 with spaces between them. The finger portions extend distally (with respect to the bladder 12') and are shaped and positioned to engage portions of the heart of opposite sides of the right pulmonary veins RPV and left pulmonary veins LPV, the veins being received in the spaces between the finger portions. Each of the finger portions has on its tip an eyelet 304' with a hole 305' to which an inserter wire can be attached for use in guiding the bladder and tube into the desired position.

Retention of each of the embodiments can be further enhanced, after insertion and extension by supplying air to the tube, by filling the tube with a light-weight particulate material, such as tiny plastic spheres. The particulate material can be introduced through the respective conduit 32, 62, 32' by blowing it in with a gas. The particulate material is essentially non-compressible, has limited fluidity, and accordingly, causes the tube to become semi-rigid, and provides for stable frictional engagement of the tube walls with the outer wall of the epicardium of the heart and the inner wall of the pericardium. In the case of the embodiment of FIG. 6, the stabilizing of the finger portions 306, 307 and 308 by the particulate material is especially beneficial to providing a grip on superior aspects of the heart and better defining the spaces for the pulmonary veins. The particulate material that fills the tube portion 302' extending along the wall of the bladder 12' tends to make that portion behave as a spine, which bridges the bladder in the proximo-distal direction with respect to the tube 28' and increases the stability of the bladder in that direction.

Figure 7:
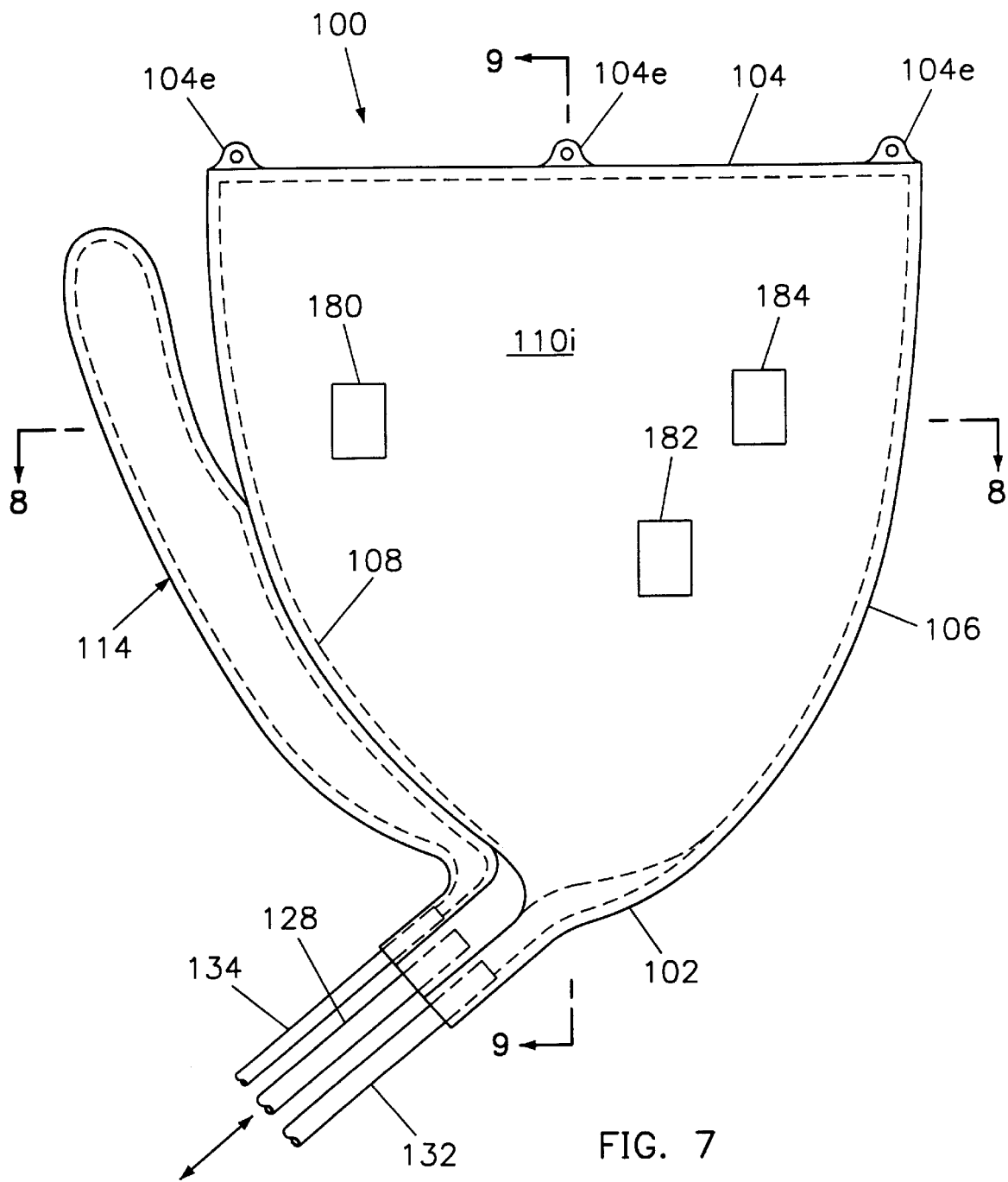
FIG. 7 is a plan view of a fourth embodiment of a bladder.
Figure 8:
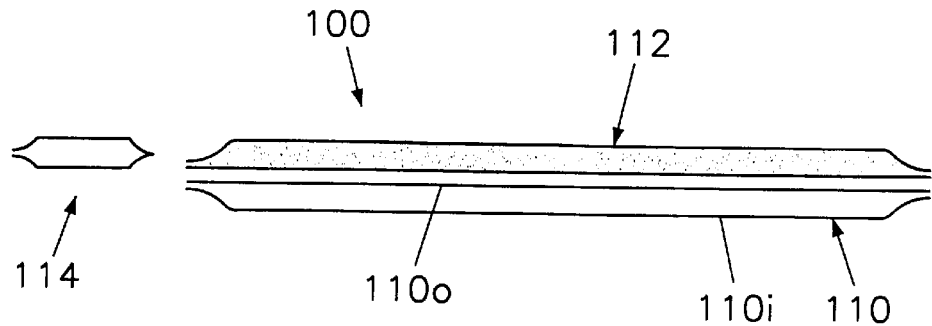
FIGS. 8 and 9 are cross-sectional views of the fourth embodiment, taken along the lines 8—8 and 9—9 of FIG. 7, respectively.
Figure 9:
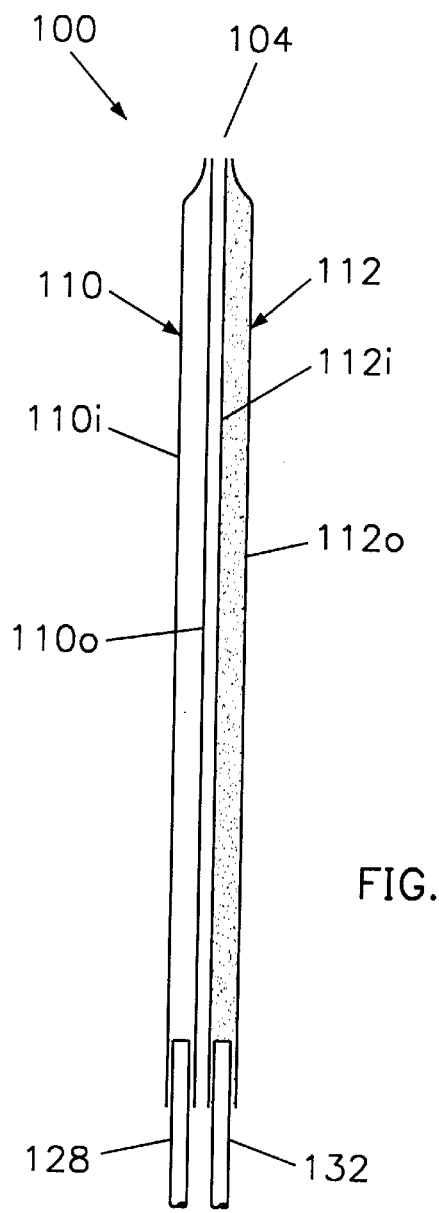

Another embodiment of the present invention, as shown in FIGS. 7 to 9, includes a bladder assembly 100. As in the other embodiments, the bladder assembly 100 is shaped generally as a part of a cone such that its proximal, narrow end 102 is located just below the apex of the heart. The distal edge 104 is of a length such that when the bladder is in place, the upper end extends circumferentially around the upper portion of the left ventricle of the heart at a position proximate to the atrio-ventricular groove through from about 180 degrees to about 270 degrees, one end being located near the pulmonary artery and the other end near the inferior vena cava. The anterior and posterior side edges 106 and 108 are configured to lie along the anterior and posterior junctures between the right and left ventricles.

The bladder assembly has two main bladders 110 and 112, which are coextensive with each other. The inner bladder 110, which engages the heart, has an inner wall panel 110i of a fluid-impermeable, flexible, extensible material, such that it can distend and apply pressure to the left ventricle. The outer wall panel 110o is of a fluid-impermeable, flexible non-extensible material. The inner and outer walls panels are joined along their edges to form a chamber. The outer bladder 112 has inner and outer wall panels 112i and 112o of fluid-impermeable, flexible non-extensible material and are joined along their edges. The edges of the two bladders are joined to each other, the dashed lines in FIG. 7 representing the bonded and sealed edges between the wall panels of the respective bladders and between the edges of the two bladders. The two bladders 110 and 112 may, of course, share a common intermediate wall. A semi-rigid tube 128 and 132 is received in sealed and bonded relation within a tubular neck portion of the respective bladders 110 and 112.

The inner wall panel 110i of the inner, pumping bladder 110 is, preferably, constructed so as to have greater elasticity at the proximal portion adjacent the heart apex and a lesser elasticity adjacent the distal portion so that the proximal portion extends more readily that the distal portion. Accordingly, as a gas is pumped into the pumping bladder to assist the left ventricle in pumping blood, the lower portion of the left ventricle is squeezed first and to a greater extent than the upper portion, thus pushing blood upwardly from adjacent the apex at the beginning of pumping assistance. The variation in elasticity of the inner wall can be attained in various ways, such as by making the inner panel 110i up from several sub-panels of varying elasticity, which can be of the same material but of varying thicknesses or of different materials with different elasticities. It is also possible to add plies of the same material to the distal portions of the inner wall. A single panel with varying thickness is preferred for the inner wall.

The bladder assembly 100 of FIGS. 7 to 9 also has a narrow elongated third bladder 114, which is joined to the edges of the bladders 110 and 122 along a portion of the lateral edge 108 that lies along the posterior aspect of the heart. The bladder 114 is located and configured so that when it is inflated it resides in the oblique sinus of the heart. A semi-rigid tube 134 is attached in sealed relation to a neck portion of the third bladder 114.

Figure 10:
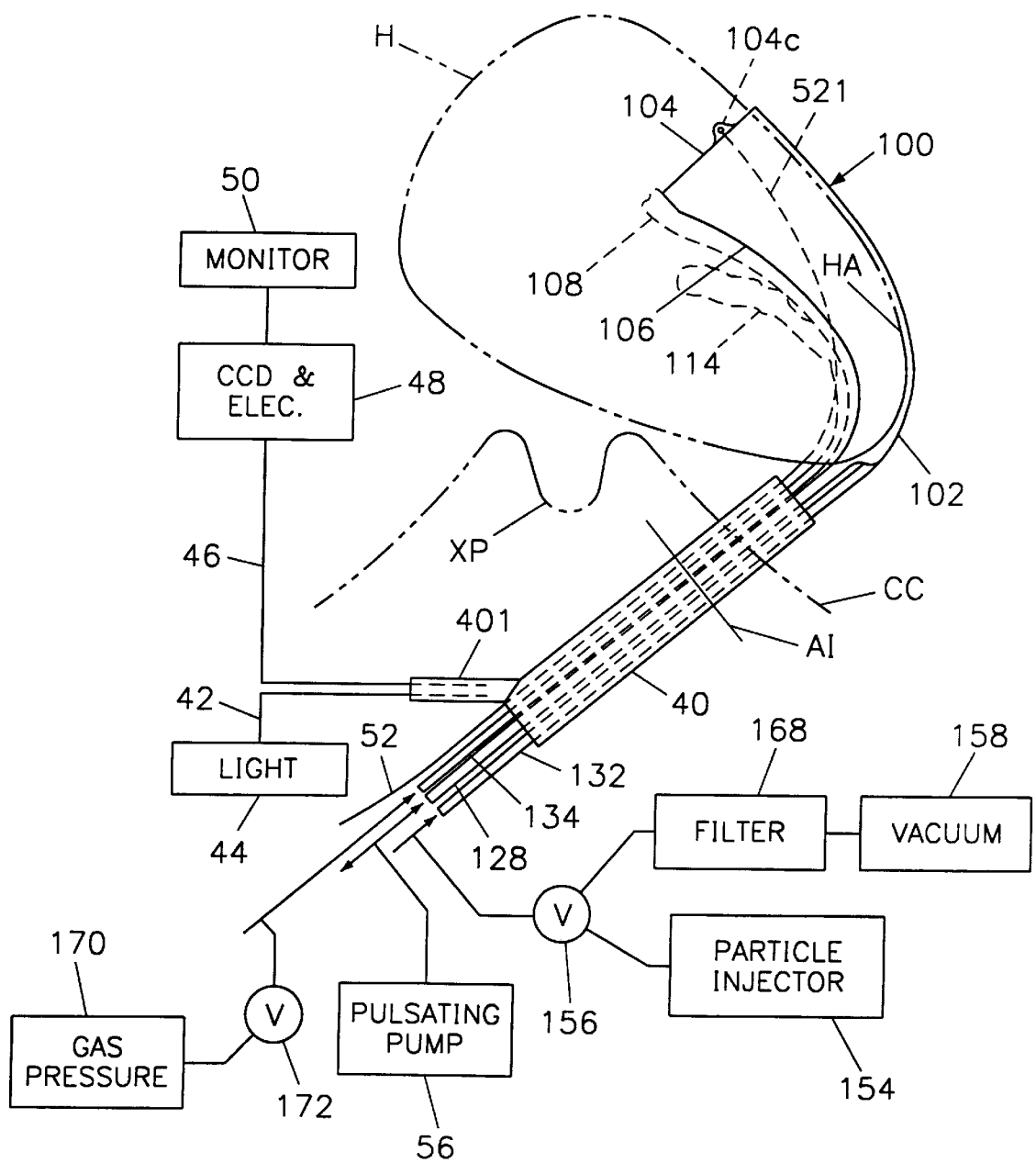
FIG. 10 is a schematic view of apparatus for carrying out the method, as used with the fourth embodiment of a bladder.

The manner of placement of the bladder assembly 100 is, for the most part, the same as that described above and shown in FIG. 5. Therefore, the schematic drawing of FIG. 10 uses the reference numerals that are applied to FIG. 5 to designate the same parts. The main differences are as follows:

After the bladder assembly 100 is placed between the heart A and the pericardium and is deployed about the heart, which is accomplished with the aid of inserter wires (e.g., 521) that are attached to eyelets 104 on the distal edge of the bladder assembly, a light-weight particulate material (described above) entrained in a gas is injected through the tube 132 into the outer bladder 112 by a particle injector 54, which may be a disposable pressure bottle containing the particles and a gas. The connection to the tube 132 of the outer bladder 112 is then changed, by switching a three-way valve 156, to a vacuum source 158, which may be a container in which a vacuum was previously drawn or a vacuum pump. The outer bladder 112 is partially evacuated of gas, the particulate material being retained in the bladder and the tube by a filter 160. Partial evacuation of the outer bladder compacts the particles and renders the outer bladder 112 semi-rigid. During the cyclical pressurizing and emp-tying of the inner bladder 110 and the resulting assistance of the left ventricle in pumping blood from the heart and in filling, the outer bladder 112 supports the reaction load during blood pumping and holds the bladder assembly 100 in place. The tubes 132, 128 and 134 are suitably secured outside the patient's body, and the relatively stiff outer bladder, the portion of which adjacent the apex is held against being pushed away from the heart by the tubes, together with the pericardium which the outer bladder engages, provides a firm support for the inner bladder 110 that resists being pushed downwardly away from the heart.

Either before or after the outer bladder is filled with packed particles, a gas under pressure is introduced from a source 170 into the third bladder 114 through the tube 134. After the third bladder is inflated, the pressure is trapped in it by closing a valve 172. The pressurized third bladder 114 is engaged in the oblique sinus and holds the bladder assembly 100 in place circumferentially.

A pacing electrode 180, a defibrillator electrode 182, and a common electrode 184 are affixed to the inner wall 110i of the inner bladder 112. Wires (not shown) lead from each electrode along the inner wall of the bladder assembly and along the tubes to outside the patient's body.

I claim:

1. Cardiac ventricular assist apparatus adapted to be placed between the pericardium and the heart by insertion through an incision in the wall of the upper abdomen below the rib cage and an incision in the inferior aspect of the pericardium proximate to the heart apex comprising a bladder assembly having walls of flexible material, the bladder assembly being of a size and shape adapted to be engageable exclusively with a substantial portion of the outer surface of the left ventricle of a heart and having a distal edge of a length adapted to extend around the heart proximate to the atrio-ventricular groove through an angle of from about 180 degrees to about 270 degrees from one end near the pulmonary artery to another end near the inferior vena cava and the bladder assembly being adapted to be passed in a collapsed condition through the incision in the pericardium to a position between the pericardial sac and the epicardium, the bladder assembly having a first bladder having an inner wall engageable with the heart;

a second bladder attached to and substantially coextensive with the first bladder;

at least one wall of the second bladder being substantially non-extensible so as to provide dimensional stability to the bladder assembly circumferentially and axially of the heart;

a tube attached to the first bladder through which a gas can be introduced into and withdrawn from the first bladder so as to apply pumping assistance to the left ventricle; and a tube attached to the second bladder through which fluid material can be introduced into the second bladder to render the second bladder substantially rigid.

2. Ventricular assist apparatus according to claim 1 wherein the first bladder has an inner wall of an elastically extensible material attached along an outer perimeter to the wall of non-extensible material of the second bladder.

3. Ventricular assist apparatus according to claim 2 wherein the elasticity of the inner wall of the first bladder is greater in a portion adjacent the distal end of the assembly than in a portion adjacent a proximal end of the bladder assembly such that a proximal portion of the first bladder enlarges before a distal portion and the assembly exerts a pumping action on the heart that is directed upwardly toward the left ventricular outflow tract.

4. Ventricular assist apparatus according to claim 1 wherein the first and second bladders have walls that are configured as segments of conical surfaces that approximately match the shape of the part of the heart that the bladder assembly engages without wrinkling.

5. Ventricular assist apparatus according to claim 1 wherein the first and second bladders have a common posterior lateral edge positioned to reside adjacent the posterior margin of the left ventricle and the bladder assembly has a third narrow elongated bladder having a proximal portion attached to a proximal portion of posterior lateral edge of the first and second bladders, the third portion being shaped and configured to be received in the oblique sinus of the heart, and further comprising a tube attached to the third bladder through which a fluid can be introduced into the third bladder so as to expand the third bladder into engagement with the oblique sinus and impede circumferential displacement of the bladder assembly relative to the heart.

6. Ventricular assist apparatus according to claim 1 and further comprising an introducer tube and an inserter wire adapted to be passed through the introducer tube and having a distal end attached to the distal edge of the bladder assembly and having a length such that it is adapted to extend out of the proximal end of the introducer tube for manipulation to move the bladder through the incision in the pericardium and into position between the epicardium and the pericardium.

7. Ventricular assist apparatus according to claim 1 and further comprising means received through the introducer tube for conducting light through the introducer tube to illuminate a portion of the pericardium and means received through the introducer tube for transmitting an image of the illuminated portion of the pericardium through the introducer tube to its proximal end.

8. Ventricular assist apparatus according to claim 1 and further comprising a sensing/pacing electrode attached to a wall of the bladder assembly that engages the heart.

9. A method of providing mechanical assistance to a failing heart comprising the steps of making an incision in the upper abdomen inferior to the xiphoid process and medial to the border of the left coastal arch;

inserting an introducer tube through the abdominal incision;

guiding the introducer tube to a position proximate to the medial aspect of the heart apex;

illuminating a portion of the pericardium proximate to the medial aspect of the heart apex and forming on a monitor an image of said portion;

making an incision in said portion of the pericardium;

providing in collapsed condition a bladder assembly having walls of flexible material, the bladder assembly being of a size and shape adapted to be engageable exclusively with a substantial portion of the outer surface of the left ventricle of a heart and having a distal edge of a length adapted to extend around the heart proximate to the atrio-ventricular groove through an angle of from about 180 degrees to about 270 degrees from one end near the pulmonary artery to another end near the inferior vena cava and the bladder assembly being adapted to be passed in a collapsed condition through the incision in the pericardium to a position between the pericardial sac and the epicardium, the bladder assembly having a first bladder having an inner wall engageable with the heart, a second bladder attached to and substantially coextensive with the first bladder, at least one wall of the first bladder being substantially non-extensible so as to provide dimensional stability to the bladder assembly circumferentially and axially of the heart, a first tube attached to the first bladder, and a second tube attached to the second bladder;

moving the collapsed bladder assembly through the pericardial incision and guiding it along the heart to a predetermined position;

deploying the collapsed bladder to engage it with the left ventricle;

introducing a fluid material into the second bladder through the second tube, the fluid material being capable of making the second bladder semi-rigid; and repeatedly pumping a gas under pressure into the bladder and withdrawing the gas from the bladder to compress and release the left ventricle.

10. A method according to claim 9 wherein the fluid material introduced into the second bladder is a particulate material entrained in a gas and wherein at least part of the gas is removed from the second bladder so as to pack the particulate material into a semi-rigid body in the second bladder.

11. A method according to claim 9 wherein the first bladder has an inner wall of an elastically extensible material attached along an outer perimeter to the wall of non-extensible material of the second bladder.

12. A method according to claim 11 wherein the elasticity of the inner wall of the first bladder is greater in a portion adjacent the distal end of the assembly than in a portion adjacent a proximal end of the bladder assembly such that a proximal portion of the first bladder enlarges before a distal portion and the assembly exerts a pumping action on the heart that is directed upwardly toward the left atrium.

13. A method according to claim 12 wherein the wherein the first and second bladders have walls that are configured as segments of conical surfaces that approximately match the shape of the part of the heart that the bladder assembly engages without wrinkling.

14. A method according to claim 13 wherein the first and second bladders have a common posterior lateral edge positioned to reside adjacent the posterior margin of the left ventricle, the bladder assembly has a third narrow elongated bladder having a proximal portion attached to a proximal portion of posterior lateral edge of the first and second bladders, the third portion being shaped and configured to be received in the oblique sinus of the heart, and a third tube is attached to the third bladder through which a fluid can be introduced into the third bladder so as to expand the third portion into engagement with the oblique sinus and impede circumferential displacement of the bladder assembly relative to the heart, and wherein a gas under pressure is introduced into the third bladder through the third tube and is maintained during the pumping action of the first bladder.

15. A method according to claim 11 wherein the bladder assembly is moved and guided by attaching at least one inserter wire to the distal edge of the bladder assembly and manipulating a portion of the wire outside of the introducer tube.

* * * * *